US00PP22194P2

(12) United States Plant Patent
van Kleinwee

(10) Patent No.: US PP22,194 P2
(45) Date of Patent: Oct. 11, 2011

(54) *PETUNIA* PLANT NAMED 'PETDERO'

(50) Latin Name: *Petunia hybrida*
Varietal Denomination: Petdero

(75) Inventor: Theodorus Cornelis Maria van Kleinwee, Enkhuizen (NL)

(73) Assignee: Syngenta Crop Protection AG, Basel (CH)

( * ) Notice: Subject to any disclaimer, the term of this patent is extended or adjusted under 35 U.S.C. 154(b) by 0 days.

(21) Appl. No.: 12/802,500

(22) Filed: Jun. 8, 2010

(51) Int. Cl.
*A01H 5/00* (2006.01)

(52) U.S. Cl. ..... Plt./356.22

(58) Field of Classification Search ..... Plt./356.22
See application file for complete search history.

*Primary Examiner* — June Hwu
(74) *Attorney, Agent, or Firm* — S. Matthew Edwards

(57) ABSTRACT

A new *Petunia* plant named 'Petdero' particularly distinguished by the large, bold red-purple flowers, good floriferousness, medium green foliage, early flowering with a good center flowering habit, and exceptional branching with outwardly spreading plant habit.

1 Drawing Sheet

Latin name of the genus and species of the plant claimed: *Petunia hybrida.*

Varietal denomination: 'Petdero'.

BACKGROUND OF THE NEW PLANT

The present invention comprises a new *Petunia*, botanically known as *Petunia hybrida*, and hereinafter referred to by the variety name 'Petdero'.

'Petdero' is a product of a planned breeding program. The new cultivar has large, bold red-purple flowers, good floriferousness, medium green foliage, early flowering with a good center flowering habit, and exceptional branching with outwardly spreading plant habit.

'Petdero' originated from a hybridization made in August 2004 in a controlled breeding environment in Enkhuizen, Netherlands. The female parent was the proprietary, unpatented plant designated 'D1314-1', with dark rose flowers.

The male parent of 'Petdero' was the proprietary, unpatented plant designated 'C1328-1', with pink flowers. The resultant seed was sown in February 2005.

'Petdero' was selected as one flowering plant within the progeny of the stated cross in the May 2005 in a controlled environment in Enkhuizen, Netherlands.

The first act of asexual reproduction of 'Petdero' was accomplished when vegetative cuttings were propagated from the initial selection in May 2005 in a controlled environment in Enkhuizen, Netherlands.

BRIEF SUMMARY OF INVENTION

Horticultural examination of plants grown from cuttings of the plant initiated in May 2005, and continuing thereafter, has demonstrated that the combination of characteristics as herein disclosed for 'Petdero' are firmly fixed and are retained through successive generations of asexual reproduction.

'Petdero' has not been observed under all possible environmental conditions. The phenotype may vary significantly with variations in environment such as temperature, light intensity and day length.

A Plant Breeder's Right for this cultivar was applied for in Canada on Feb. 9, 2010 (#10-6826). 'Petdero' has not been made publicly available more than one year prior to the filing of this application.

The following traits have been repeatedly observed and are determined to be basic characteristics of the new variety. The combination of these characteristics distinguishes this *Petunia* as a new and distinct variety.

BRIEF DESCRIPTION OF THE PHOTOGRAPHS

The accompanying photographic drawing shows typical flower and foliage characteristics of 'Petdero' with colors being as true as possible with an illustration of this type. The photographic drawing shows a flowering potted plant of the new variety and a close-up of the flowers growing in a 4 inch pot.

DETAILED BOTANICAL DESCRIPTION

The plant descriptions, measurements and aforementioned photographs were taken in Gilroy, Calif. from plants growing California from plants growing in a greenhouse trial in April 2010. These plants were approximately 13-14 weeks of age.

Color references are made to The Royal Horticultural Society Colour Chart (R.H.S.) 2001.

TABLE 1

DIFFERENCES BETWEEN THE NEW VARIETY 'PETDERO' AND A SIMILAR VARIETY

| | 'Petdero' | 'Petrosena' (U.S. Plant Pat. No. 18,498) |
|---|---|---|
| Flowering response: | Earlier | Later |
| Branching/trailing habit: | More/more | Fewer/less |
| Flower color (general): | RHS N74A | RHS N66A |
| Foliage size: | Little smaller | Little larger |
| Foliage shape: | Ovate | Broadly elliptical |

Plant:

*Form, growth and habit.*—Initially upright, later on more trailing and outwardly spreading, good branching habit, pinching enhances development of lateral branches.

*Plant height.*—11-12 cm.
*Plant height (inflorescence included).*—About 20 cm.
*Plant width.*—50-55 cm.
*Garden performance and tolerance to weather.*—Very good.
*Crop time to flowering.*—About 8-9 weeks.

Roots:
*Number of days to initiate roots and produce a rooted cutting.*—18-23 days at about 22 degrees C.
*Type.*—Fine, fibrous, free branching.
*Color.*—RHS N155B but whiter.

Foliage:
*Arrangement.*—Alternate, upper leaves sub-opposite.
*Immature, leaf color, upper surface.*—RHS 137B.
*Lower surface.*—Closest to RHS 137D.
*Mature, leaf color, upper surface.*—RHS 137B.
*Lower surface.*—Closest to RHS 137D.
*Length.*—4.5-5.5 cm.
*Width.*—2.4-3.0 cm.
*Shape.*—Ovate.
*Base shape.*—Attenuate.
*Apex shape.*—Broadly acute.
*Margin.*—Entire.
*Texture, upper surface.*—Glandular hairs.
*Lower surface.*—Glandular hairs.
*Color of veins, upper surface.*—RHS 144B.
*Color of veins, lower surface.*—RHS 144B.
*Petiole color.*—RHS 144B.
*Length.*—0.5-1.0 cm.
*Diameter.*—0.3 cm.
*Texture.*—Glandular hairs.

Stem:
*Color of stem.*—Closest to RHS 146B.
*Length of stem.*—25-30 cm.
*Diameter.*—0.3 cm.
*Length of internodes.*—2.0-2.5 cm.
*Texture.*—Glandular hairs; pilose.
*Color of peduncle.*—Closest to RHS 146B.
*Length of peduncle.*—2.5-3.0 cm.
*Peduncle diameter.*—0.15 cm.
*Texture.*—Glandular hairs; pilose.

Inflorescence:
*Type.*—Flowers appear solitary in upper leaf axis.
*Floret type.*—Funnel-shaped; 5 lobed petals; fused at the base; calyx, 5 deeply lobed sepals.
*Blooming habit.*—Continuous throughout the growing season. Good floriferousness.
*Quantity of inflorescences per plant.*—About 100.
*Lastingness of individual blooms on the plant.*—5-7 days.
*Fragrance.*—Slightly sweet.

Bud (just before opening/showing color):
*Color.*—RHS 187A.
*Length.*—2.5-3.5 cm.
*Width.*—0.5 cm.
*Shape.*—Oblong.

Immature inflorescence:
*Diameter.*—4.5 cm.
*Color, upper surface.*—Closest to RHS N74A but much darker and velvety looking.
*Lower surface.*—Closest to RHS N77CB.

Mature inflorescence:
*Floret horizontal diameter.*—5.3-5.5 cm.
*Vertical depth.*—3.0-3.5 cm.
*Petal color, upper surface.*—Closest to RHS N74A; RHS 59B mid-veins.
*Lower surface.*—Closest to RHS 75D basally, RHS N74C at the margins; RHS 144A to RHS 144B mid-veins.
*Petal apex shape.*—Mucronulate.
*Petal base shape.*—Fused.
*Petal margin.*—Entire.
*Waviness of petals.*—Moderate.
*Petal lobation.*—Moderate.
*Petal texture, upper surface.*—Papillose.
*Under surface.*—Papillose.
*Corolla tube color inside.*—RHS 155B suffused with RHS 155C; RHS 166A and RHS 165A veins.
*Outside.*—RHS 155B to RHS 155C; RHS 144A mid-veins; RHS 195A to RHS 195B veins.
*Corolla tube length.*—2.0 cm.
*Corolla texture, inside.*—Papillose.
*Outside.*—Long glandular hair; pilose.

Calyx:
*Quantity of sepals.*—5.
*Color, upper surface.*—RHS 137B.
*Lower surface.*—RHS 137C.
*Length.*—1.5 cm.
*Width.*—0.3 cm.
*Shape.*—Oblong.
*Apex shape.*—Obtuse.
*Based.*—Fused.
*Margins.*—Entire.
*Texture, upper surface.*—Glandular hairs.
*Lower surface.*—Glandular hairs.

Reproductive organs:
*Pistil.*—1.
*Length.*—1.6 cm.
*Style color.*—RHS 145C.
*Style length.*—1.5 cm.
*Stigma color.*—RHS 145A.
*Stigma shape.*—Oval.
*Ovary color.*—RHS 143B.
*Stamens.*—5.
*Color of filaments.*—RHS 155B.
*Length filaments.*—1.4-1.6 cm.
*Anther color.*—RHS 155A.
*Anther length.*—0.2 cm.
*Anther shape.*—Oval.
*Color of pollen.*—RHS 155B.
*Pollen amount.*—Good.
*Fertility/seed set.*—Has not been observed on this hybrid.

Disease/pest resistance: Disease/pest resistance has not been observed on this hybrid.

What is claimed is:

1. A new and distinct variety of *Petunia* plant named 'Petdero' substantially as illustrated and described herein.

* * * * *

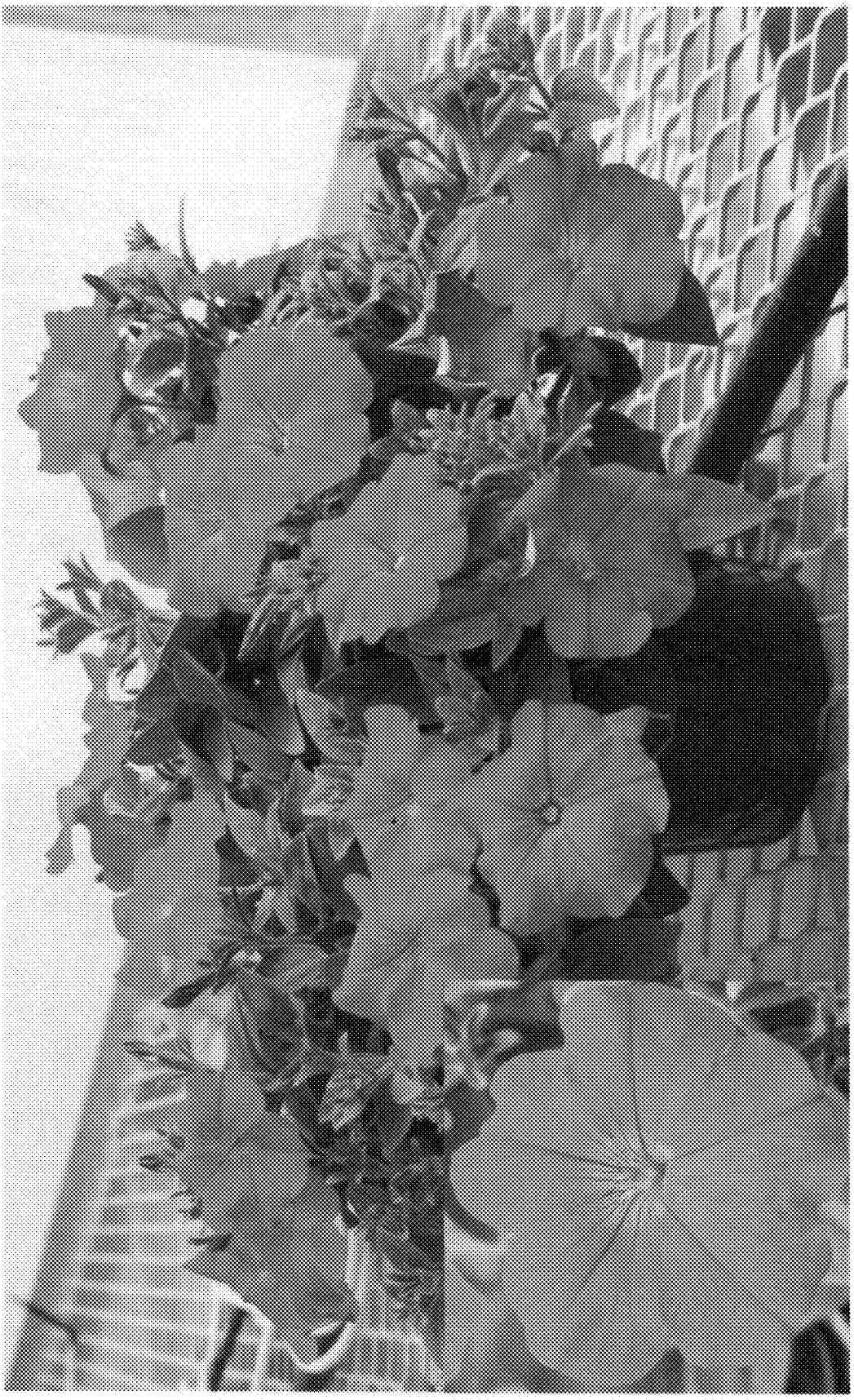

UNITED STATES PATENT AND TRADEMARK OFFICE

CERTIFICATE OF CORRECTION

PATENT NO. : PP22,194 P2
APPLICATION NO. : 12/802500
DATED : October 11, 2011
INVENTOR(S) : Theodorus Cornelis Maria van Kleinwee It is certified that error appears in the above-identified patent and that said Letters Patent is hereby corrected as shown below:

At column 3, line 59, delete "RHS N77CB" and insert therefor --RHS N77B--

Signed and Sealed this
Twenty-second Day of November, 2011

David J. Kappos

David J. Kappos
*Director of the United States Patent and Trademark Office*